(12) United States Patent
Sung et al.

(10) Patent No.: US 9,138,491 B2
(45) Date of Patent: Sep. 22, 2015

(54) HIGH-SENSITIVITY MAGNETIC RESONANCE IMAGING NANO-CONTRAST AGENT BASED ON AN ANIONIC POLYMER AND CATIONIC POLYMER ION COMPLEX, AND A PRODUCTION METHOD THEREFOR

(75) Inventors: Moon-Hee Sung, Daejeon (KR); Yong Taik Lim, Daejeon (KR); Young-Woock Noh, Daejeon (KR); Il Han Lee, Daejeon (KR); Hyun Min Kim, Daejeon (KR)

(73) Assignees: BIOLEADERS CORPORATION, Daejeon (KR); THE INDUSTRY AND ACADEMIC COOPERATION IN CHUNGNAM NATIONAL UNIVERSITY, Daejeon (KR); KOOKMIN UNIVERSITY INDUSTRY-ACADEMIC COOPERATION FOUNDATION, Seoul (KR)

( * ) Notice: Subject to any disclaimer, the term of this patent is extended or adjusted under 35 U.S.C. 154(b) by 109 days.

(21) Appl. No.: 14/110,138

(22) PCT Filed: Apr. 7, 2011

(86) PCT No.: PCT/KR2011/002433
§ 371 (c)(1),
(2), (4) Date: Jan. 7, 2014

(87) PCT Pub. No.: WO2012/137999
PCT Pub. Date: Oct. 11, 2012

(65) Prior Publication Data
US 2014/0170077 A1    Jun. 19, 2014

(30) Foreign Application Priority Data

Apr. 6, 2011 (KR) ........................ 10-2011-0031665

(51) Int. Cl.
*A61K 49/12* (2006.01)
*A61B 5/055* (2006.01)
*A61K 49/18* (2006.01)

(52) U.S. Cl.
CPC ........... *A61K 49/126* (2013.01); *A61K 49/1863* (2013.01); *A61K 49/1872* (2013.01)

(58) Field of Classification Search
CPC ....... A61K 49/00; A61K 49/06; A61K 49/12; A61B 5/055
USPC ..................... 424/9.322, 9.323, 9.4
See application file for complete search history.

(56) References Cited

U.S. PATENT DOCUMENTS

| 4,338,158 | A | 7/1982 | Bentvelzen | |
| 5,532,350 | A | 7/1996 | Cottrell et al. | |
| 6,048,515 | A * | 4/2000 | Kresse et al. | 424/9.322 |
| 2004/0247655 | A1 | 12/2004 | Asmus et al. | |
| 2007/0202075 | A1 | 8/2007 | Hadba et al. | |
| 2008/0152615 | A1 | 6/2008 | Sung et al. | |
| 2009/0180966 | A1* | 7/2009 | Borbely et al. | 424/9.36 |

FOREIGN PATENT DOCUMENTS

| EP | 1723855 B1 | 11/2006 |
| KR | 10-2007-0046681 A | 5/2007 |
| KR | 10-0862973 B1 | 10/2008 |
| KR | 10-2009-0008838 A | 1/2009 |

OTHER PUBLICATIONS

Chen, Z., et al, "Biocompatible Nanocomplexes for Molecular Targeted MRI Contrast Agent", "Nanoscale Res Lett", Mar. 18, 2009, pp. 618-626, vol. 4.
Lee, J., et al, "Artificially engineered magnetic nanoparticles for ultra-sensitive molecular imaging", "Nature Medicine", Dec. 24, 2006, pp. 95-99, vol. 13, No. 1.
Lin, Y., et al., "Preparation of Nanoparticles Composed of Chitosan/Poly-gamma-glutamic Acid and Evaluation of Their Permeability through Caco-2 Cells", "Biomacromolecules", Jan. 22, 2005, pp. 1104-1112, vol. 6.
Lu, J. et al. "Manganese ferrite nanoparticle micellar nanocomposites as MRI contrast agent for liver imaging", "Biomaterials", Feb. 20, 2009, pp. 2919-2928, vol. 30.
Na, H., et al., "Inorganic Nanoparticles for MRI Contrast Agents", "Adv. Mater.", 2009, pp. 2133-2148, vol. 21.
Saboktakin, M., et al., "Synthesis and characterization of superparamagnetic chitosan-dextran sulfate hydrogels as nano carriers for colon-specific drug delivery", "Carbohydrate Polymers", Mar. 4, 2010, pp. 372-376, vol. 81.
Sun, C., et al., "Magnetic Nanoparticles in MR Imaging and Drug Delivery", "Adv Drug Deliv Rev.", Aug. 17, 2008, pp. 1252-1265, vol. 60, No. 11.

* cited by examiner

*Primary Examiner* — Michael G Hartley
*Assistant Examiner* — Jagadishwar Samala
(74) *Attorney, Agent, or Firm* — Hultquist, PLLC; Steven J. Hultquist (57) ABSTRACT

The present invention relates to a nano-composite containing anionic and cationic polymers and a method for preparing thereof, and more particularly to a poly-gamma-glutamic acid (γ-PGA)/chitosan/manganese iron oxide nanoparticle composite prepared by encapsulating iron oxide-based nanoparticles in a γ-PGA/chitosan polymer composite using the ionic self-assembly properties of poly-gamma-glutamic acid (γ-PGA) and chitosan, which are biocompatible polymer materials, and to a method for preparing thereof.
The present invention provides a magnetic resonance imaging nano-contrast agent based on a nanoparticle composite including iron oxide-based nanoparticles encapsulated in a self-assembled composite of anionic poly-gamma-glutamic acid (γPGA) and cationic chitosan. The iron oxide-based nanoparticles encapsulated in the composite interact with each other to produce a synergistic effect on the amplification of magnetic resonance signals, and thus have an relatively excellent contrast effect compared to when they exist as single particles.

6 Claims, 5 Drawing Sheets

HIGH-SENSITIVITY MAGNETIC RESONANCE IMAGING NANO-CONTRAST AGENT BASED ON AN ANIONIC POLYMER AND CATIONIC POLYMER ION COMPLEX, AND A PRODUCTION METHOD THEREFOR

CROSS-REFERENCE TO RELATED APPLICATIONS

This application is a U.S. national phase under the provisions of 35 U.S.C. §371 of International Patent Application No. PCT/KR11/02433 filed Apr. 7, 2011, which in turn claims priority of Korean Patent Application No. 10-2011-0031665 filed Apr. 6, 2011. The disclosures of such international patent application and Korean priority patent application are hereby incorporated herein by reference in their respective entireties, for all purposes.

TECHNICAL FIELD

The present invention relates to a nano-composite containing anionic and cationic polymers and a method for preparing thereof, and more particularly to a poly-gamma-glutamic acid (γ-PGA)/chitosan/manganese iron oxide nanoparticle composite prepared by encapsulating iron oxide-based nanoparticles in a γ-PGA/chitosan polymer composite using the ionic self-assembly properties of poly-gamma-glutamic acid (γ-PGA) and chitosan, which are biocompatible polymer materials, and to a method for preparing thereof.

BACKGROUND ART

Magnetic resonance imaging (MRI) is a technique that obtains images by placing the human body inside a large magnet tube that generates a magnetic field, resonating hydrogen atom nucleus in the body by generating high frequency waves, measuring the differences in signals from various tissues of the body, and reconstituting the signals. Namely, it is to obtain images by giving high frequency waves to the body in the large magnet tube to generate a signal like echo from the human body and converting the signal into digital information.

Magnetic resonance imaging (MRI) has an important advantage in that it is actually harmless to the human body, because it uses high frequency waves that are non-ionizing radiations, unlike simple X-ray imaging or computer tomography (CT). Also, because MRI uses a magnetic field harmless to the human body and high frequency waves that are non-ionizing radiations, it has an excellent contrast for soft tissues without a contrast agent, compared to CT and enables to obtain information on the biochemical characteristics of tissues containing hydrogen atom nuclei. Although MRI is similar to CT in that it shows cross-sectional images, MRI also has an advantage in that images of the human body in a desired direction among a horizontal axis direction, a longitudinal axis direction, a diagonal direction and the like can be easily obtained without changing the patient's posture, whereas, in CT, images of the human body in a horizontal axis direction are mainly obtained.

However, because the water content of the human body is 70% or more and the difference in the concentration between portions of the human body is also insignificant, the sensitivity of images in a process of imaging MRI signals is low, and thus MRI shows limitations in distinguishing between normal tissue and abnormal tissue in the same organ and has a shortcoming in that early diagnosis of disease is not easy.

MRI contrast agents are auxiliary materials that increase the sensitivity of magnetic resonance imaging by maximizing the difference in signals and have been widely used in clinical applications. MRI contrast agents are largely classified into $T_1$ and $T_2$ contrast agents. $T_1$ has the effect of causing a labeled portion to appear lighter than the surrounding tissue, whereas $T_2$ has the effect of causing a labeled portion darker than the surrounding tissue. $T_1$ contrast agents that are currently typically used in clinical applications include gadolinium ions ($Gd^{2+}$), and $T_2$ contrast agents include iron oxide nanoparticles.

In recent years, studies using an MRI contrast agent have been actively conducted in which a specific site of the human body is labeled and the developmental process thereof is observed with time or in which a specific cell or foreign material is labeled and injected into the human body, and then the migration pathway thereof is investigated. This provides clues to enable to establish the causes of diseases, which have not been established, or to establish processes of treating diseases using novel drugs or metabolic procedures.

Typical contrast agents based on iron oxide nanoparticles, which are currently used in clinical applications, are obtained by dissolving ferrous chloride hydrate ($FeCl_2.H_2O$) and ferric chloride hydrate ($FeCl_3.H_2O$) in an aqueous solution and reducing iron ions by inducing a basic solution. Dextran that is a kind of polysaccharide is added to form a coating film on the surface of the iron oxide nanoparticles in order to maintain the stability of the particles. The nanoparticles synthesized by the above manner have an advantage of excellent biocompatibility, but have a low effect on the amplification of magnetic resonance signals, because of their small particle size and low surface crystallinity. In addition, the nanoparticles have a shortcoming in that they do not have a functional group capable of chemically binding to a target ligand for selectively labeling a specific site in the human body. As a result, it is difficult to form target-specific particles, and the contrast effect of the particles is not sufficient to sense a cellular or molecular target.

Recently, as an alternative material for iron oxide nanoparticles synthesized by the aqueous solution method, iron oxide nanoparticles synthesized at high temperature in an organic solvent have been receiving attention. In this synthesis method, the formation of iron ion particles at high temperature occurs slowly, and thus the particles formed have a very uniform size and shape and a very high surface crystallinity. In addition, there is an advantage in that the size of the nanoparticles can be easily controlled by changing either the amount of a surfactant that is added to stabilize the particles during synthesis or the reaction temperature. In recent years, nanoparticles having a significantly improved signal amplification effect as a result of adding a transition metal such as manganese or cobalt to iron oxide particles have been reported. However, because these nanoparticles are synthesized in an organic solvent, they are hydrophobic in nature. For this reason, in order to inject these nanoparticles into the human body, the phase of the nanoparticles should necessarily be transferred to an aqueous phase. For this purpose, methods are used in which the surface of hydrophobic nanoparticles is coated with an amphipathic phospholipid or a biodegradable polymer material having a hydrophobic group chemically introduced therein. However, such methods have many problems in terms of the stability and biocompatibility of the particles.

US Patent Publication No. 20090180966 discloses a method for preparing nanoparticles comprising anions and cations that form ionic bonds with each other, the method comprising complexing anionic and cationic polymers with metal ions serving as contrast agents for magnetic resonance imaging. However, the nanoparticles prepared by this method have a disadvantage in that the sensitivity of magnetic resonance imaging signals is significantly lower than that of signals obtained using nanoparticle contrast agents for magnetic resonance imaging. In addition, there is a disadvantage in that the metal ions are actually difficult to use as contrast agents for magnetic resonance imaging, because the toxicity thereof is very strong.

Accordingly, the present inventors have made extensive efforts to prepare a nano-contrast agent for magnetic resonance imaging using the ionic self-assembly properties of poly-gamma-glutamic acid (γPGA) and chitosan, which are biocompatible polymer materials, and as a result, have found that, when iron oxide-based nanoparticles are encapsulated in a complex of poly-gamma-glutamic acid (γPGA) and a chitosan polymer, they effectively increase magnetic resonance signals to increase the label sensitivity of a specific cell or organ in the human body, thereby completing the present invention.

DISCLOSURE OF INVENTION

Technical Problem

It is an object of the present invention to provide a method for preparing a nanoparticle composite containing a magnetic resonance imaging nano-contrast agent encapsulated in a composite of an anionic polymer and a cationic polymer, in which iron oxide-based nanoparticles are encapsulated in a composite of poly-gamma-glutamic acid (γPGA) and a chitosan polymer so that they effectively increase magnetic resonance signals to increase the label sensitivity of a specific cell or organ in the human body.

Technical Solution

To achieve the above object, the present invention provides a method for preparing a nanoparticle composite containing a magnetic resonance imaging nano-contrast agent encapsulated in a polymer composite formed by an ionic bond between an anionic polymer and a cationic polymer, wherein the method comprising the steps of: (a) obtaining an anionic polymer/magnetic resonance imaging nano-contrast composite by mixing an organic solvent solution containing the anionic polymer with an organic solvent solution containing the magnetic resonance imaging nano-contrast agent; and (b) obtaining the nanoparticle composite containing the magnetic resonance imaging nano-contrast agent encapsulated in the polymer composite formed by an ionic bond between the anionic polymer and the cationic polymer by adding the cationic polymer to the obtained anionic polymer/magnetic resonance imaging nano-contrast composite.

The present invention also provides a nano-particle composite, prepared by the above method, wherein the nano-particle composite contains a magnetic resonance imaging nano-contrast agent encapsulated in a polymer composite formed by an ionic bond between an anionic polymer and a cationic polymer.

BEST MODE FOR CARRYING OUT THE INVENTION

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

In one aspect, the present invention is directed to a method for preparing a nanoparticle composite containing a magnetic resonance imaging nano-contrast agent encapsulated in a polymer composite formed by an ionic bond between an anionic polymer and a cationic polymer, wherein the method comprising the steps of: (a) obtaining an anionic polymer/magnetic resonance imaging nano-contrast composite by mixing an organic solvent solution containing the anionic polymer with an organic solvent solution containing the magnetic resonance imaging nano-contrast agent; and (b) obtaining the nanoparticle composite containing the magnetic resonance imaging nano-contrast agent encapsulated in the polymer composite formed by an ionic bond between the anionic polymer and the cationic polymer by adding the cationic polymer to the obtained anionic polymer/magnetic resonance imaging nano-contrast composite.

In the present invention, the anionic polymer may be selected from the group consisting of polyglutamic acid, polyacrylic acid, alginate, carrageenan, hyaluronic acid, poly(styrene sulfonate), carboxymethylcellulose, cellulose sulfate, dextran sulfate, heparin, heparin sulfate, poly(methylene-co-guanidine), and condroitin sulfate.

The present invention is directed to a method for coating iron oxide-based nanoparticles using an ionic interaction between an anionic polymer and a cationic polymer, which are biocompatible materials. Poly-gamma-glutamic acid that is used in the present invention is an ultra-high-molecular-weight natural amino acid polymer material biosynthesized by *Bacillus subtilis* derived from Chungkookjang, a Korean traditional fermented food, and has excellent biocompatibility and biodegradability. It is classified as an anionic polymer due to a large amount of carboxyl groups present in glutamic acid, an amino acid constituting it. It is highly reactive with cationic minerals, and thus can be used in various applications, including food additives, health functional foods, cosmetic products, and medical drugs. Particularly, it has an excellent effect of encapsulating hydrophobic drugs or useful proteins, and thus studies on the use thereof in drug delivery systems have been actively conducted. Herein, in order to ensure the stability of the encapsulated material, gelation-induced nanoparticles can be formed by inducing the self-assembly of poly-gamma-glutamic acid with chitosan that is a cationic polymer.

In the present invention, the cationic polymer may be selected from the group consisting of chitosan, poly(ethylenimine), poly(L-lysine), poly(diallyldimethyl ammonium chloride), poly(allylamine), hydrochloride, poly-ornithine, poly(vinylamine)hydrochloride, poly(2-(dimethylamino) ethyl methacrylate), poly(amido amine), dendrimer, and gelatin.

Chitosan that is used as a cationic polymer in the present invention is a natural animal dietary fiber derived from crustaceans such as shrimps or crabs and is a cationic polymer material that carries positive charges in a dissolved state. Chitosan consisting of glucosamine bonds has a similar molecular structure to that of human body tissue, and thus is highly compatible with the human body and cause no immune rejection. Thus, it is used in various applications, including foods and medical drugs.

In the present invention, the nano-contrast agent for magnetic resonance imaging may be selected from a nanoparticle group consisting of iron (Fe), manganese (Mn), cobalt (Co), gadolinium (Gd), praseodymium (Pr), samarium (Sm), europium (Eu), terbium (Tb), dysprosium (Dy), holmium (Ho), erbium (Er), thulium (Tm), ytterbium (Yb), lutetium (Lu), and composites thereof.

In the present invention, the nano-contrast agent for magnetic resonance imaging consists of iron oxide nanoparticles showing magnetic resonance imaging contrast effects. In an example of the present invention, manganese-doped iron oxide ($MnFe_2O_4$) nanoparticles were used, wherein the manganese is synthesized in an organic solvent, and these nanoparticles were stabilized by a surfactant consisting of short hydrocarbon chains, and thus are hydrophobic in nature.

An embodiment of the present invention provides a nanoparticle composite prepared by using PGA as an anionic polymer, chitosan as a cationic polymer, and iron oxide-based nanoparticles as a magnetic resonance imaging nano-contrast agent, and encapsulating the iron oxide-based nanoparticles in a γ-PGA/chitosan composite. But, it will be obvious to a person having ordinary skill in the art that the anionic polymer may be selected from the group consisting of poly-glutamic acid, polyacrylic acid, alginate, carrageenan, hyaluronic acid, poly(styrene sulfonate), carboxymethylcellulose, cellulose sulfate, dextran sulfate, heparin, heparin sulfate, poly(methylene-co-guanidine), and condroitin sulfate, the cationic polymer may be selected from the group consisting of chitosan, poly(ethylenimine), poly(L-lysine), poly(diallyldimethyl ammonium chloride), poly(allylamine), hydrochloride, poly-ornithine, poly(vinylamine)hydrochloride, poly(2-(dimethylamino)ethyl methacrylate), poly(amido amine), dendrimers, and gelatin, and the nano-contrast agent for magnetic resonance imaging may be selected from a nanoparticle group consisting of iron (Fe), manganese (Mn), cobalt (Co), gadolinium (Gd), praseodymium (Pr), samarium (Sm), europium (Eu), terbium (Tb), dysprosium (Dy), holmium (Ho), erbium (Er), thulium (Tm), ytterbium (Yb), lutetium (Lu), and composites thereof (Hyon Bin Na. et al., *Advanced Materials*, 21:2133, 2009; Conroy Sun. et al., *Advanced Drug Delivery Reviews*, 60:1252, 2008; Jian Lu. et al., *Biomaterials*, 30:2919, 2009; J. Lee. et al., *Nature Medicine*, 13:95, 2007).

In another aspect, the present invention is directed to a nano-particle composite, prepared by the above method, wherein the nano-particle composite contains a magnetic resonance imaging nano-contrast agent encapsulated in a polymer composite formed by an ionic bond between an anionic polymer and a cationic polymer.

In another embodiment of the present invention, in order to develop a magnetic resonance imaging nano-contrast agent showing an excellent effect on the amplification of magnetic resonance signals by encapsulating iron oxide-based nanoparticles in a composite of poly-gamma-glutamic acid (γPGA) and chitosan, which are biocompatible natural polymers, iron oxide-based nanoparticles were coated with poly-gamma-glutamic acid (γPGA) having a high molecular weight (500 kDa), and the phase transfer thereof from an organic phase to an aqueous phase was induced. Then, in order to ensure the uniformity and stability of the particles and introduce an amine group that is a functional group making it easy to introduce a target-specific ligand, the surface of the particles was coated with chitosan once more. Herein, the poly-gamma-glutamic acid (γPGA) and the chitosan were formed into a composite by simple ionic self-assembly without any chemical modification in order to further increase the biocompatibility thereof. In addition, a significant number of iron oxide-based nanoparticles could be encapsulated in the poly-gamma-glutamic acid (γPGA)/chitosan composite by using the high-molecular-weight poly-gamma-glutamic acid (γPGA). The present invention has significantly increased contrast effect compared to when they exist as single particles, as the iron oxide-based nanoparticles encapsulated in the composite through ionic assembly using anionic poly-gamma-glutamic acid. (γPGA) and cationic chitosan interact with each other and a synergistic effect on the amplification of magnetic resonance signals is induced.

In still another embodiment of the present invention, as iron oxide nanoparticles showing magnetic resonance imaging contrast effects, manganese-doped iron oxide ($MnFe_2O_4$) nanoparticles were used, wherein the manganese is synthesized in an organic solvent, and these nanoparticles were stabilized by a surfactant consisting of short hydrocarbon chains, and thus are hydrophobic in nature. The particles are spherical particles that are uniformly dispersed in an organic solvent and have a diameter of about 8 nm. In order to transfer the phase of the manganese-doped iron oxide ($MnFe_2O_4$) nanoparticles to an aqueous phase, the nanoparticles were coated with a poly-gamma-glutamic acid (γPGA) having a molecular weight of 500 kDa. The poly-gamma-glutamic acid (γPGA) has a gamma-polypeptide structure formed by an amide bond between the gamma-carboxyl group and alpha-amino group of glutamic acid, and the alpha-amino group is exposed, and thus the poly-gamma-glutamic acid (γPGA) is anionic in nature. The alpha-amino group attacks the surface of the iron oxide nanoparticles to push out the hydrogen surfactant and form bonds on the surface. Because some of the carboxyl groups are exposed to the outside without forming a bond, the coated surface carries negative charges. When cationic chitosan is added to the manganese-doped iron oxide ($MnFe_2O_4$) nanoparticles coated with poly-gamma-glutamic acid (γPGA), a spherical polymer composite is formed by ionic interaction. Chitosan is a material obtained by deacetylating chitin consisting of N-acetyl-D-glucosamine units, and in the present invention, chitosan having a molecular weight of about 50 kDa and a deacetylation degree of about 80% was used. Glutaraldehyde functions to crosslink the amine groups of chitosan to increase the bonding strength between the chains. In addition, when a small amount of poly(ethylene glycol) is added to the particle surface, the particles are pegylated, and thus the blood half-life of the particles is increased by improved stability and solubility due to pegylation of the particles and preventing the uptake of the particles by reticuloendothelial system (RES) cells.

As used herein, the term "MRI relaxivity" refers to a value indicating the extent to which the $T_1$ or $T_2$ relaxation time decreases based on the unit concentration of a magnetic element (i.e., iron (Fe) or manganese (Mn)) contained in nanoparticles. It is a numerical value indicating the ability of a contrast agent to amplify a magnetic resonance signal and is expressed as $r_2$ for $T_2$ contrast agents.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

Preparation of Reagents and Particles

Example 1-1

Preparation of Reagents

Iron (III) acetylacetonate and manganese (II) actylacetonate as starting materials were allowed to react in the organic solvent 1-octadecene at high temperature, thereby synthesizing manganese-doped iron oxide nanoparticles ($MnFe_2O_4$). Herein, in order to stabilize the nanoparticles, the surfactant oleic acid was added. In addition, poly-gamma-glutamic acid (γPGA) having a molecular weight of 500 kDa (BioLeaders, Korea), chitosan having a molecular weight of 50 kDa (MIRAE BIOTECH, Korea), and PEG-NHS (SunBio, Korea) were prepared.

Example 1-2

Process for Phase Transfer of Iron Oxide Nanoparticles

Poly-gamma-glutamic acid (PGA) (molecular weight: 500 kDa) was dissolved in a DMSO solvent at a concentration of 10 mg/ml, and manganese-doped iron oxide ($MnFe_2O_4$) nanoparticles were dispersed in chloroform at a concentration of 10 mg/ml. The two solutions were bubbled with nitrogen gas in a closed container for 10 minutes or more, and then mixed with each other in an amount of 10 ml for each solution. The mixed solution was stirred at a temperature of 60° C. for 2 hours, thereby preparing a poly-gamma-glutamic acid/manganese-doped iron oxide ($MnFe_2O_4$) nanoparticle composite. In order to remove the remaining surfactant and reaction impurities from the solution, a mixed organic solvent of (hexane:ethanol:chloroform=2:1:1) was added to the prepared composite, after that, the solution was centrifuged at 5000 rpm for 10 minutes, and then, the supernatant was discarded, and the precipitate was allowed to stand in a desiccator in a vacuum state for about one day to completely remove the remaining organic solvent. Then, about 20 ml of 50 mM $NaHCO_3$ solution was added to the resulting composite, after that, the resulting solution was vortexed until the remaining precipitate was completely dissolved. The vortexted solution was sonicated and filtered through a 0.2 μm cellulose filter (Adventec).

Example 1-3

Formation of Poly-Gamma-Glutamic Acid (γPGA)/Iron Oxide Nanoparticle/Chitosan Composite by Ionic Bonding Chitosan was dissolved in an aqueous solution at a concentration of 10 mg/ml, and 10 ml of water was added to 3 ml of the chitosan solution with stirring. Then, 1 ml of the poly-gamma-glutamic acid/manganese iron oxide ($MnFe_2O_4$) nanoparticle solution prepared in Example 1-2 was added thereto using a pipette. The mixture was stirred at 600 rpm for 2 hours, and 10 ml of glutaraldehyde was added thereto, followed by stirring for 1 hour. The quantification of amine groups in the aqueous solution of the poly-gamma-glutamic acid (γPGA)/chitosan/manganese iron oxide ($MnFe_2O_4$) nanoparticle composite was performed by the nynhydrin method. Herein, a L-lysine solution was used as a standard solution.

Example 1-4

Pegylation of Poly-Gamma-Glutamic Acid (γPGA)/Chitosan/Iron Oxide Nanoparticle Composite PEG-NHS was dissolved in triple-distilled water at a molar concentration twice that of amine groups contained in the poly-gamma-glutamic acid (γPGA)/chitosan/manganese iron oxide ($MnFe_2O_4$) nanoparticle composite prepared in Example 1-3, and the two solution were mixed with each other at a volume ratio of 1:1, and then stirred for about 12 hours. In order to remove unreacted polymer material and NHS, the stirred mixture was centrifuged at 5000 rpm for about 10 minutes, the supernatant was discarded, and the precipitate was dispersed again in triple-distilled water, and then centrifuged once more, thereby purifying the composite. The size of the poly-gamma-glutamic acid (γPGA)/chitosan/manganese iron oxide ($MnFe_2O_4$) nanoparticle composite was observed by DLS, TEM and SEM.

Figure 1:
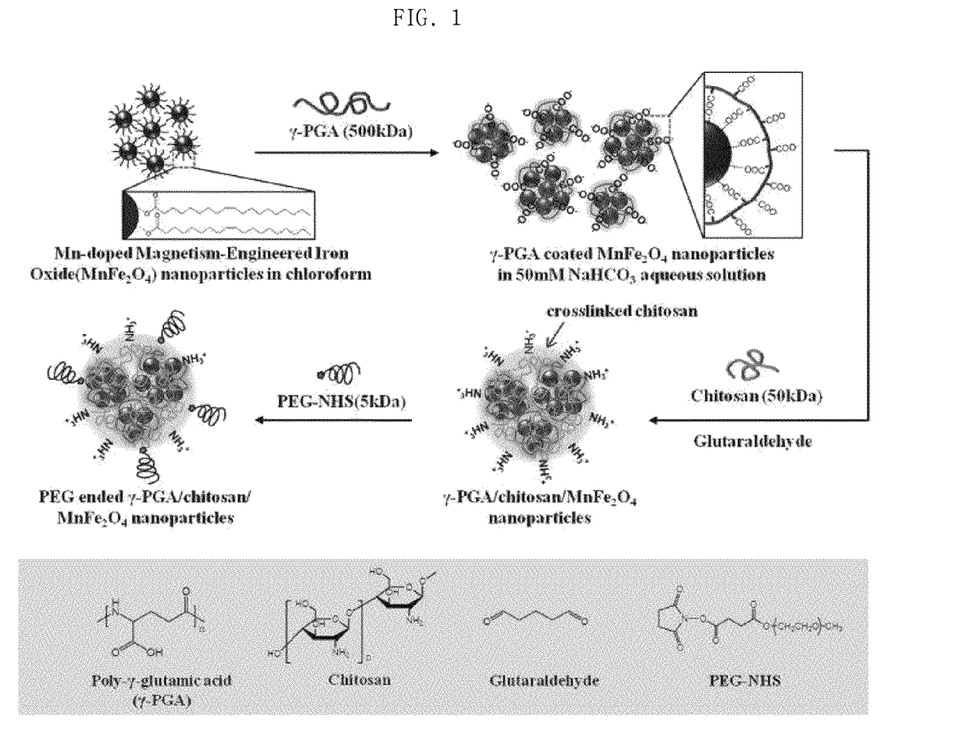
FIG. 1 shows a method for synthesizing a poly-gamma-glutamic acid (γPGA)/chitosan composite having iron oxide-based nanoparticles encapsulated therein.
Figure 2:
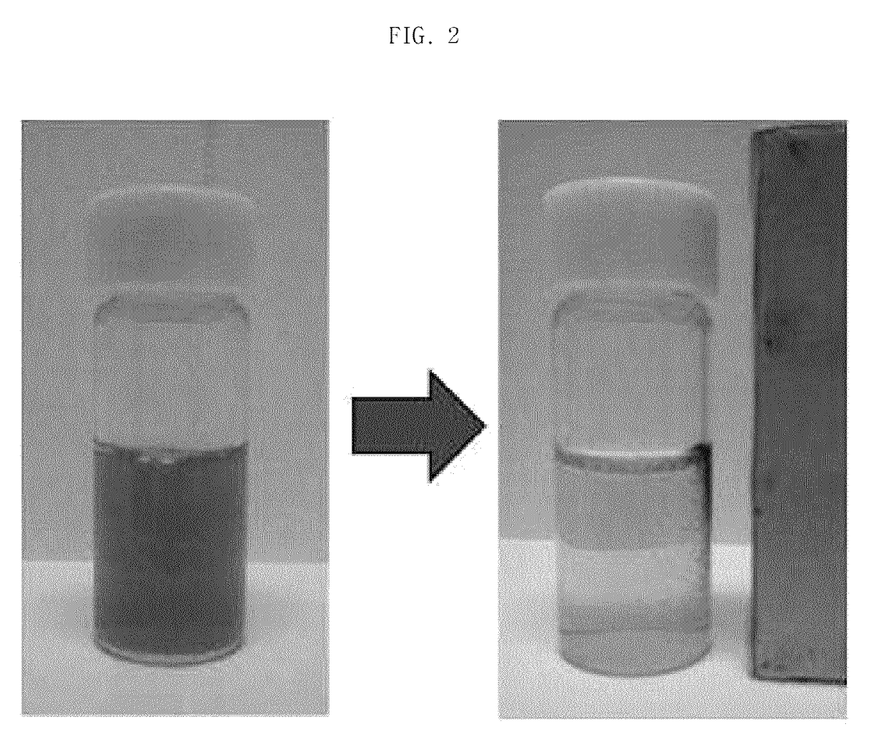
FIG. 2 shows the magnetic property of iron oxide-based nanoparticles with time when putting a permanent magnet aside a poly-gamma-glutamic acid (γPGA)/chitosan/iron oxide-based nanoparticle composite dispersed in an aqueous solution.
Figure 3:
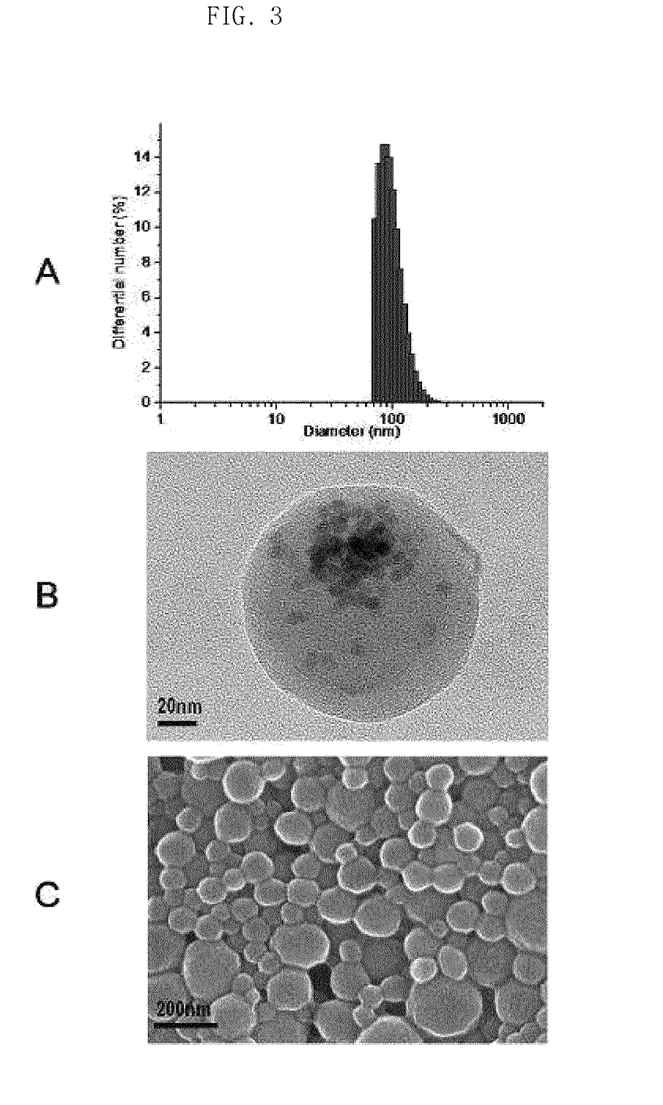
FIG. 3 shows the size of a poly-gamma-glutamic acid (γPGA)/chitosan/iron oxide-based nanoparticle composite, measured by DLS (see FIG. 3A), the internal shape and particle size of a PGA/chitosan composite having iron oxide nanoparticles encapsulated therein, observed by TEM (see FIG. 3B), and the particle size and uniformity of the composite, observed by SEM (see FIG. 3C).

As a result, it could be seen that the particle size measured by DLS was 90-200 nm (see FIG. 3($a$)). This size is suitable for EPR effect (enhanced permeation and retention effect) when being injected into the human body and has the property of targeting abnormal tissues.

The particle size and the inside of the composite were observed by TEM, and as a result, it was shown that a significant number of manganese-iron oxide nanoparticles were encapsulated in the spherical poly-gamma-glutamic acid (γPGA)/chitosan polymer composite (see FIG. 3($b$)). Thus, as described above, a synergistic effect can be seen, which is that the manganese-iron oxide nanoparticles interact with each other in the polymer composite and amplify the MRI signals effectively.

In addition, the surface shape and size of the particles were observed by SEM, and as a result, spherical particles having a size of about 90-200 nm, similar to the particle size measured by DLS, could be observed (see FIG. 3($c$)).

Example 2

Measurement of Activity of Poly-Gamma-Glutamic Acid (γPGA)/Chitosan/Manganese Iron Oxide ($MnFe_2O_4$) Nanoparticle Composite

Example 2-1

Measurement of MRI Relaxivity of Poly-gamma-Glutamic Acid (γPGA)/Chitosan/Manganese Iron Oxide ($MnFe_2O_4$) Nanoparticles The MRI relaxivity of the poly-gamma-glutamic acid (γPGA)/chitosan/manganese iron oxide ($MnFe_2O_4$) nanoparticle composite solution prepared in Example 1-3 was measured using 4.7T MRI for small animals, and the quantification of iron and manganese elements in the solution was measured by ICP-AES.

Figure 4:
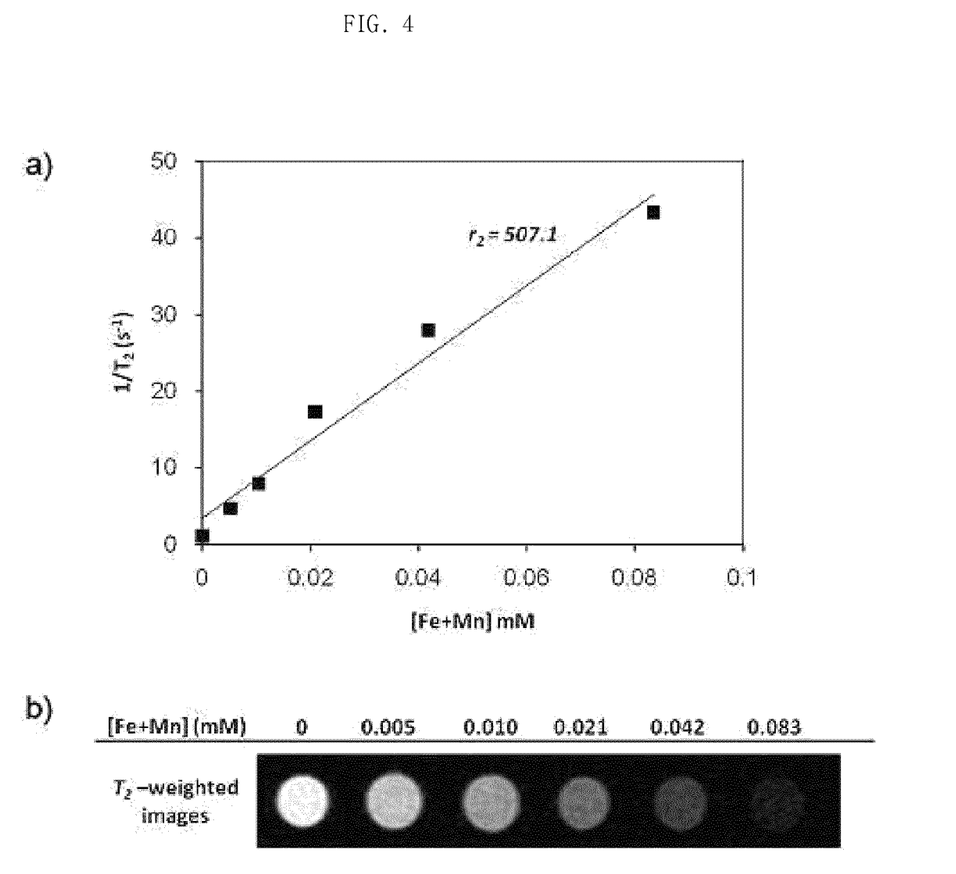
FIG. 4 shows the effect of a poly-gamma-glutamic acid (γPGA)/chitosan/iron oxide-based nanoparticle composite on the amplification of MRI signals.

As a result, it could be seen that the $r_2$ value of the poly-gamma-glutamic acid (γPGA)/chitosan/manganese iron oxide ($MnFe_2O_4$) nanoparticle composite was about 507(Fe+Mn) $mM^{-1}s^{-1}$, which was at least four times greater than the $r_2$ value of commercialized dextran-based iron oxide particles synthesized in an aqueous solution (see FIG. 4).

Example 2-2

Intracellular Delivery of Poly-Gamma-Glutamic Acid (γPGA)/Chitosan/Manganese Iron Oxide ($MnFe_2O_4$) Nanoparticle Composite An experiment for the intracellular delivery of the nanoparticle composite, prepared in Example 2-1, into HeLa cancer cells, was performed. The cells were treated with 25 μg/ml of the particles, and then stained with prussian blue to determine whether the particles were delivered into the cells.

Figure 5:
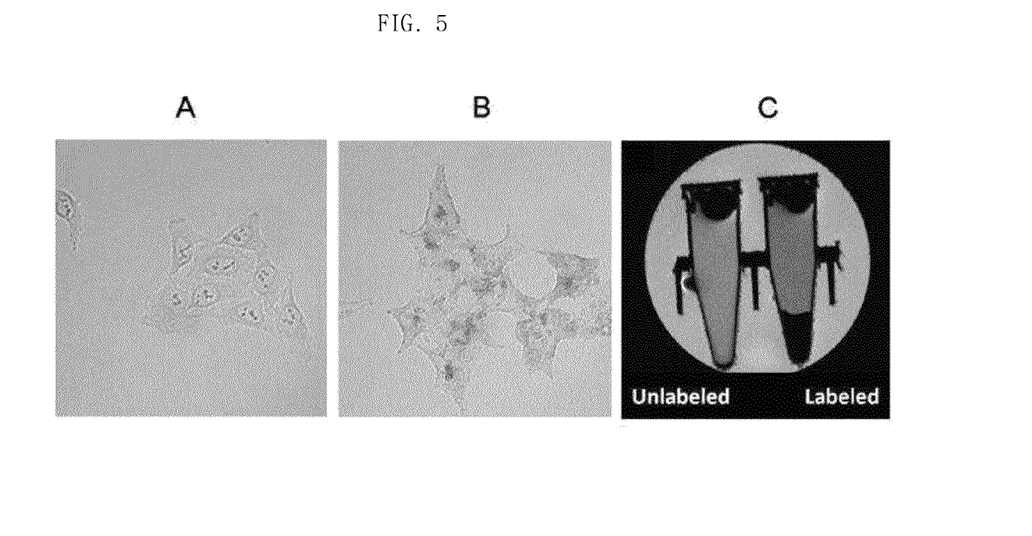
FIG. 5 shows the results obtained by treating cells with a poly-gamma-glutamic acid (γPGA)/chitosan/iron oxide-based nanoparticle composite and staining the treated cells with prussian blue to determine whether the particles were delivered into the cells, and shows the ability of the composite to label cells in MRI.

The surface of the poly-gamma-glutamic acid (γPGA)/chitosan/manganese iron oxide ($MnFe_2O_4$) nanoparticle composite carries positive charges due to the amine group of chitosan and easily adheres to the cell membrane that generally carries negative charges so that it is easily delivered into cells. Because of such characteristics, cells were treated with 25 μg/ml of the particles, and then stained with prussian blue to determine whether the particles were delivered into the cells (see FIG. 5).

Example 2-3

MRI Imaging of Cells Labeled with Poly-Gamma-Glutamic Acid (γPGA)/Chitosan/Manganese Iron Oxide ($MnFe_2O_4$) Nanoparticle Composite The cells treated with the particles in Example 2-2 were collected, and MRI images thereof could be obtained using a 4.7T MRI system for small animals. The cells labeled with the poly-gamma-glutamic acid (γPGA)/chitosan/manganese iron oxide ($MnFe_2O_4$) nanoparticle composite could be observed on the MRI images. It could be seen that unlabeled cells appeared light together with the surrounding water, whereas labeled cells appeared dark. This suggests that the poly-gamma-glutamic acid (γPGA)/chitosan/manganese iron oxide ($MnFe_2O_4$) nanoparticle composite is easily delivered into specific cells. In addition, the results of the MRI imaging indicate that the darkening effect by magnetic resonance signals is obtained even by only a small amount of the particles (see FIG. 5).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

The present invention has a significant increased contrast effect compared to when they exist as single particles, as the iron oxide-based nanoparticles encapsulated in the composite through ionic assembly using anionic poly-gamma-glutamic acid (γPGA) and cationic chitosan interact with each other and a synergistic effect on the amplification of magnetic resonance signals is induced.

The invention claimed is:

1. A method for preparing a nanoparticle composite containing a magnetic resonance imaging nano-contrast agent encapsulated in a polymer composite formed by an ionic bond between an anionic polymer and a cationic polymer, wherein the method comprises the steps of:
   (a) obtaining an anionic polymer/magnetic resonance imaging nano-contrast composite by mixing an organic solvent solution containing the anionic polymer with an organic solvent solution containing the magnetic resonance imaging nano-contrast agent and coating the anionic polymer on the magnetic resonance imaging nano-contrast agent to induce phase transfer from an organic phase to an aqueous phase; and
   (b) obtaining the nanoparticle composite containing the magnetic resonance imaging nano-contrast agent encapsulated in the polymer composite formed by an ionic bond between the anionic polymer and the cationic polymer by adding the cationic polymer to the obtained anionic polymer/magnetic resonance imaging nano-contrast composite;
   wherein the anionic polymer is selected from the group consisting of polyglutamic acid, polyacrylic acid, alginate, carrageenan, hyaluronic acid, poly(styrene sulfonate), carboxymethylcellulose, cellulose sulfate, heparin, heparin sulfate, poly(methylene-co-guanidine), and condroitin sulfate.

2. The method according to claim 1, wherein the cationic polymer is selected from the group consisting of chitosan, poly(ethylenimine), poly(L-lysine), poly(diallyldimethyl ammonium chloride), poly(allylamine), hydrochloride, poly-ornithine, poly(vinylamine)hydrochloride, poly(2-(dimethylamino)ethyl methacrylate), poly(amido amine), dendrimer, and gelatin.

3. A nano-particle composite, prepared according to the method of claim 2, wherein the nano-particle composite contains a magnetic resonance imaging nano-contrast agent encapsulated in a polymer composite formed by an ionic bond between an anionic polymer and a cationic polymer.

4. The method according to claim 1, wherein the magnetic resonance imaging nano-contrast agent is selected from a nanoparticle group consisting of iron (Fe), manganese (Mn), cobalt (Co), gadolinium (Gd), praseodymium (Pr), samarium (Sm), europium (Eu), terbium (Tb), dysprosium (Dy), holmium (Ho), erbium (Er), thulium (Tm), ytterbium (Yb), lutetium (Lu), and composites thereof.

5. A nano-particle composite, prepared according to the method of claim 4, wherein the nano-particle composite contains a magnetic resonance imaging nano-contrast agent encapsulated in a polymer composite formed by an ionic bond between an anionic polymer and a cationic polymer.

6. A nano-particle composite, prepared according to the method of claim 1, wherein the nano-particle composite contains a magnetic resonance imaging nano-contrast agent encapsulated in a polymer composite formed by an ionic bond between an anionic polymer and a cationic polymer.

* * * * *